United States Patent [19]
Fallon

[11] Patent Number: 5,602,290
[45] Date of Patent: Feb. 11, 1997

[54] PRETREATMENT OF DILUTE ETHYLENE FEEDSTOCKS FOR ETHYLBENZENE PRODUCTION

[75] Inventor: Kevin J. Fallon, Boston, Mass.

[73] Assignee: Raytheon Engineers & Constructors, Inc., Lexington, Mass.

[21] Appl. No.: 453,646

[22] Filed: May 30, 1995

[51] Int. Cl.$^6$ .................................................. C07C 2/66
[52] U.S. Cl. .......................... 585/448; 585/446; 585/323; 585/310; 585/809
[58] Field of Search ...................... 585/448, 449, 585/450, 323, 310, 446, 809

[56] References Cited

U.S. PATENT DOCUMENTS

| | | | |
|---|---|---|---|
| 2,381,175 | 8/1945 | Mattox | 585/448 |
| 2,573,341 | 10/1951 | Kniel | 585/446 |
| 2,909,574 | 10/1959 | Woodle | 585/448 |
| 3,691,245 | 9/1972 | Helzner | 585/446 |
| 3,751,504 | 8/1973 | Keown et al. | 585/323 |
| 3,766,290 | 10/1973 | Carlson . | |
| 4,008,289 | 2/1977 | Ward et al. | 585/448 |
| 4,169,111 | 9/1979 | Wight . | |
| 4,479,812 | 10/1984 | Hsia et al. . | |
| 4,849,569 | 7/1989 | Smith, Jr. . | |
| 4,922,053 | 5/1990 | Waguespack et al. . | |
| 5,003,119 | 3/1991 | Sardina et al. | 585/449 |
| 5,019,143 | 5/1991 | Mehrta . | |
| 5,073,653 | 12/1991 | Butler . | |
| 5,157,180 | 10/1992 | West et al. | 585/446 |

*Primary Examiner*—Glenn A. Caldarola
*Attorney, Agent, or Firm*—Lappin & Kusmer LLP

[57] ABSTRACT

A process is disclosed for pretreating a dilute ethylene feedstock with benzene, ethylbenzene, or mixtures thereof to reduce the higher olefin content of the ethylene feedstock and to render it suitable as the feed to an alkylation reactor for producing ethylbenzene. Benzene and ethylbenzene recovery are integrated with other downstream operations in the ethylbenzene production.

36 Claims, 3 Drawing Sheets

PRETREATMENT OF DILUTE ETHYLENE FEEDSTOCKS FOR ETHYLBENZENE PRODUCTION

The present invention relates generally to improvements in the preparation of ethylbenzene from ethylene and benzene which facilitate the use of relatively inexpensive dilute ethylene feedstocks without affecting the quality of the ethylbenzene product and while minimizing the need for expensive additional upstream operations unrelated to the other operations associated with the ethylbenzene process.

BACKGROUND OF THE INVENTION

Ethylbenzene is a major commodity chemical, most notably used as a feedstock in the preparation of styrene monomer. For many years, ethylbenzene was produced by employing Lewis acids to catalyze benzene ethylation, also referred to as the Friedels Craft reaction. Commercial processes used either boron trifluoride or aluminum chloride catalysts. During the 1960s zeolites with molecular size pores were introduced as acid catalysts for petroleum processing. Their use was extended to benzene ethylation as a way to eliminate the troublesome liquid-phase Lewis acid catalysts, which caused environmental and metallurgical difficulties.

Today, therefore, it is well known in the art to prepare ethylbenzene by alkylating benzene with ethylene in the presence of a suitable catalyst. Both single and multi-bed alkylation reactors are known. For example, in U.S. Pat. No. 3,478,119 (Maier et al.), substantially anhydrous benzene is alkylated with high purity ethylene over a solid phosphoric acid catalyst. U.S. Pat. Nos. 3,591,650 (Mitsak), 3,848,012 (Applegath et al.), and 3,766,290 (Carlson) describe processes for producing ethylbenzene by reacting ethylene with benzene in the presence of an aluminum chloride catalyst. U.S. Pat. No. 3,691,245 (Helzner) describes a process for producing ethylbenzene by alkylating benzene with ethylene, further including various process embellishments such as recovering benzene in the off-gases by recirculating a large portion of the polyethylbenzene byproduct, splitting the benzene-rich polyethylbenzene scrubber effluent, and processing both benzene-rich scrubber effluent together with the total reactor effluent to recover additional benzene, ethylbenzene and residual polyethylbenzene.

In U.S. Pat. Nos. 3,751,504 (Keown et al.), 3,751,506 (Burress), and 3,755,483 (Burress), the alkylation reaction is carried out in the vapor phase in the presence of a crystalline aluminosilicate zeolite characterized by a particular x-ray diffusion pattern. A number of more recent patents in this art, such as U.S. Pat. Nos. 4,169,111 (Wight), 5,073,653 (Buffer), 4,922,053 (Waguespack et al.), and 4,849,569 (Smith), describe variations on the zeolite-catalyzed alkylation process utilizing different zeolite catalysts and/or different process parameters. The foregoing prior art patents are incorporated herein by reference.

Conventionally, as taught by the prior art, ethylene is alkylated in the presence of a large excess of benzene (e.g. 6–9 moles bezene per mole of ethylene) over a zeolite catalyst. The excess benzene is distilled from the reactor effluent and recycled to the alkylation reactor. The aforementioned processes typically utilize polymer grade (about 99.8% pure) ethylene and "nitration" grade (about 99.7% pure) benzene. Cheaper supplies of ethylene, however, are available. One widely available and economically attractive source of ethylene for preparing ethylbenzene is a dilute ethylene feedstock, such as the offgas produced by fluid catalytic cracking units in petroleum refineries or by coke ovens. Such dilute ethylene feedstocks containing for example 10–25% ethylene by volume, however, are typically contaminated with a variety of both reactive and substantially inert components. The reactive impurities of greatest concern are propylene and heavier olefins, which are highly reactive with benzene during the alkylation reaction and result in the formation of heavier alkylbenzenes which then contaminate the ethylbenzene product stream. Furthermore, these unwanted reactions consume benzene and result in unwanted byproducts which must be subsequently separated and treated to recover the benzene or else burned with recovery of energy value.

To minimize the aforementioned problems, dilute ethylene feedstocks have previously been pretreated to reduce their propylene and heavier olefin contents from several percent to levels similar to those found in polymer grade ethylene prior to utilizing such feedstocks for ethylbenzene production. But, the prior art processes for pretreating dilute ethylene feedstocks to remove higher olefin contaminants are generally expensive and require two or more separate unit operations. For example, one relatively effective pretreatment process is to absorb the unwanted higher olefin contaminants in a naphtha solvent. For effectiveness and economy, however, this process also requires a downstream step to recover volatilized naphtha from the treated gas stream, as well as a downstream step to strip the absorbed olefins from the naphtha. Prior art refrigeration processes for pretreating dilute ethylene feedstocks are also generally effective but, for efficiency, also entail several additional operations and equipment completely unrelated to the ethylbenzene production process. These processing requirements have limited the utility of dilute ethylene feedstocks in the production of ethylbenzene and raised the costs of such operations. These and other problems with and limitations of the prior art are overcome with the dilute ethylene feedstock pretreatment process of the present invention.

OBJECTIVES OF THE INVENTION

Accordingly, a principal object of this invention is to provide a process for pretreating dilute ethylene feedstocks by contact with an aromatic stream consisting of benzene, ethylbenzene, or mixtures thereof to reduce the content of higher olefins prior to the alkylation process in ethylbenzene production.

It is a specific object of this invention to provide an economical process for pretreating dilute ethylene feedstocks to reduce the propylene and other higher olefin content to less than about 0.2–5%, preferably about 0.2–2%, by volume of the ethylene content.

It is also an object of this invention to provide a process for pretreating dilute ethylene feedstocks in preparation for ethylbenzene production which utilizes only materials and compounds already present in conventional ethylbenzene operations.

Another object of this invention is to provide a process for pretreating dilute ethylene feedstocks to reduce the content of higher olefins entailing no more than one additional unit operation and which is readily integrated with conventional ethylbenzene operations.

Specifically, it is an object of this invention to provide a process wherein a dilute ethylene feedstock in an ethylbenzene process is pretreated by contact with a lean benzene stream to absorb propylene and higher olefin contaminants prior to the alkylation step.

Still another object of this invention is to provide a process wherein a dilute ethylene feedstock in an ethylbenzene process is pretreated by contact with a lean ethylbenzene stream to absorb propylene and higher olefin contaminants prior to the alkylation step.

Other objects and advantages of the present invention will in part be obvious and will in part appear hereinafter. The invention accordingly comprises the methods and processes, involving the several steps and the relation and order of one or more of such steps with respect to each of the others and to the apparatus exemplified in the following detailed disclosure and as illustrated by the drawing, and the scope of the application of which will be indicated in the claims.

SUMMARY OF THE INVENTION

The dilute ethylene pretreatment process of this invention generally comprises scrubbing a dilute ethylene feedstream by contacting it in a countercurrent absorber with "lean" benzene or "lean"0 ethylbenzene drawn at least in part from a downstream stage of an ethylbenzene production plant. It has been found that, under appropriate process conditions, benzene, ethylbenzene, and mixtures thereof will preferentially absorb propylene, butylene and other higher olefins from the dilute ethylene stream. Thus, these contaminants are substantially stripped from the ethylene feedstream rendering it suitable for alkylation to ethylbenzene. Separation of the higher olefins from the "rich" benzene, ethylbenzene, or mixed aromatic streams and recovery of the lean benzene and/or ethylbenzene for recycle is fully integrated into the ethylbenzene production process. For example, the lean benzene recovered from the rich benzene stream can be mixed with the pretreated ethylene stream in preparation for the alkylation step. Therefore, the process of this invention entails only a single additional unit operation. Benzene and ethylbenzene are already integral components of ethylbenzene production; accordingly, the pretreatment process of this invention entails no introduction of additional, foreign substances, such as a naphtha solvent, as in prior art processes. Numerous process efficiencies and economies are thus realized.

DETAILED DESCRIPTION OF PREFERRED EMBODIMENTS

Figure 1:
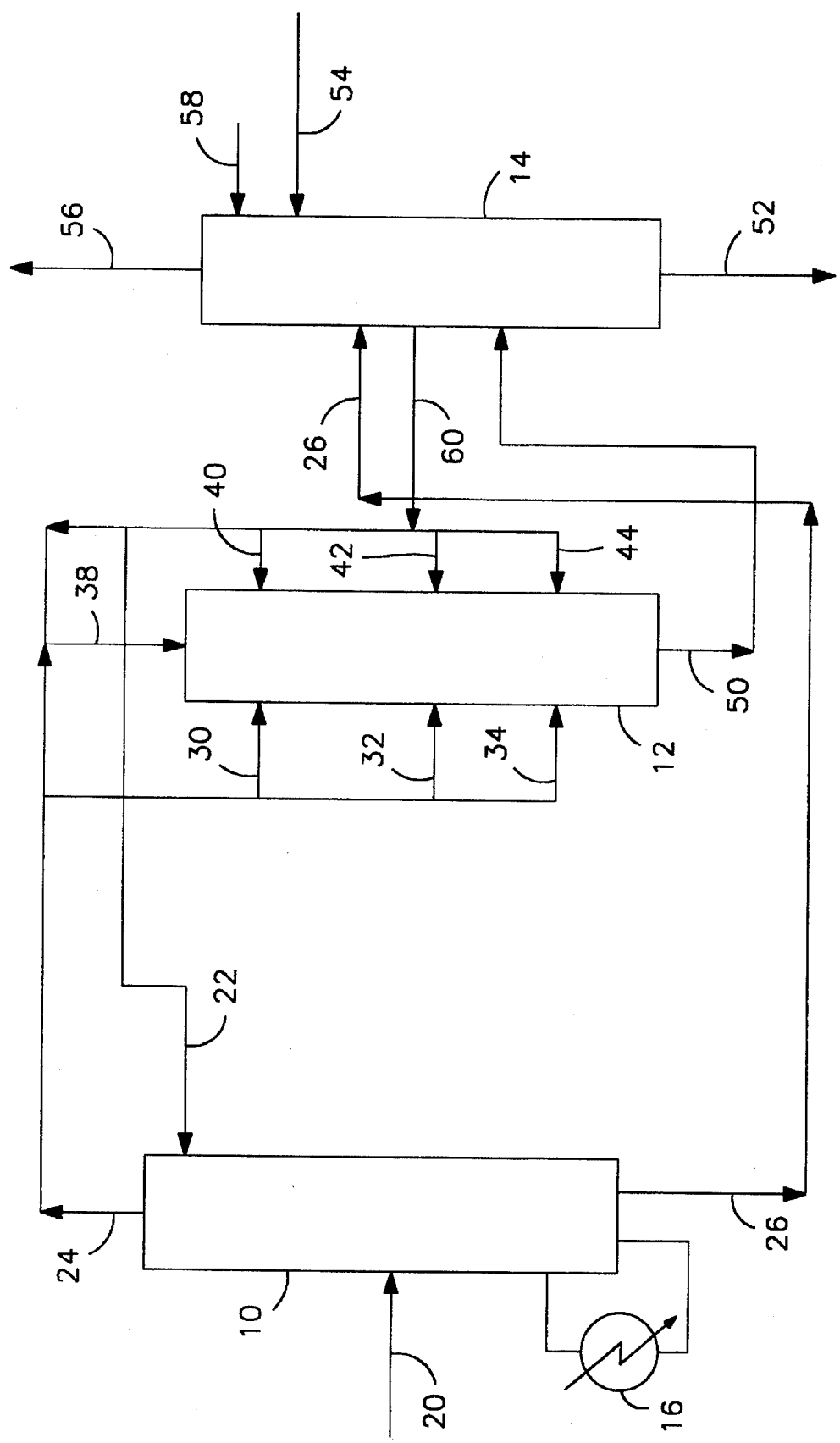
FIG. 1 is a schematic process flowchart of an ethylbenzene production process utilizing benzene for the dilute ethylene feedstream pretreatment of this invention.

The process of this invention broadly comprises pretreating a dilute ethylene feedstream with benzene, ethylbenzene, and mixtures thereof, to reduce the content of higher olefin contaminants prior to the alkylation step of an ethylbenzene process. Various integrated downstream operations facilitate recovery and recycling of the benzene and/or ethylbenzene. Referring to FIG. 1, in a first step of one embodiment of this invention, a dilute ethylene feedstock 20 is directed into an absorber column 10 where it is brought into contact with lean benzene. As used herein, the term "lean benzene" refers to benzene that is essentially free from any dissolved higher olefins, as hereinafter defined, more specifically benzene having a higher olefin content of less than about 100 parts per million by weight. Absorber 10 contains either a suitable packing material or distillation trays to maximize liquid-gas contact. Numerous suitable packing materials are well known in the art. The lean benzene is fed to absorber 10 via feedstream 22 from benzene fractionation column 14, where unreacted benzene is separated from crude ethylbenzene in a downstream operation, as discussed hereinafter. The ratio of benzene to ethylene feedstock in absorber 10 may advantageously range from about 5–50 parts by weight. An exchanger 16 is used to reboil the absorber bottoms and thus to strip ethylene from the rich benzene leaving the absorber bottoms.

Dilute ethylene feedstock 20 may be obtained from any convenient and economical source, commonly the offgas from the catalytic cracking units of petroleum refineries. This offgas will generally comprise about 10–30% by volume of ethylene together with a variety of reactive and relatively inert components. A dominant proportion of these offgas streams is typically made up of varying percentages of hydrogen, nitrogen, carbon oxides, methane, ethane, and other alkanes, all of which are substantially inert to the alkylation environment used for producing ethylbenzene. On the other hand, typically about 6% or more by volume of these offgas streams comprise propylene, butylene isomers, and other higher olefins. As used herein, the term "higher olefin" refers to any olefin comprising three or more carbon atoms. These higher olefins are highly reactive in the ethylbenzene alkylation environment, typically reacting with benzene to form $C_9$ and higher alkylaromatic compounds, such as cumene, which are close boiling to ethylbenzene and are costly to distill therefrom. The process of this invention, however, is effective in reducing the proportion of higher olefin contaminants in the dilute ethylene feedstocks to acceptable levels of about 0.2–5%, preferably about 0.2–2%, by volume of the ethylene content, and thereby correspondingly reducing contamination of the ethylbenzene product. Optimum process parameters for this absorption step, such as temperature, flowrates relative to the size of absorber 10, and proportions of benzene to ethylene feed, may all be determined by routine calculations in order to achieve the desired reduction of higher olefins in the dilute ethylene feed. For example, the temperature in absorber 10 may range from about 40° C. at the top of absorber 10 to about 325° C. at the bottoms of the absorber, for this benzene-ethylene embodiment preferably a range of 40° C. at the top to about 225° C. at the bottoms, and the pressure may range from about 100–400 psig. The absence of any alkylation catalyst in absorber 10 prevents premature alkylation.

Flowstream 24 leaving absorber 10 comprises a lean or pretreated ethylene feedstock having a reduced content of higher olefins and thus ready for feeding to alkylation reactor 12. As used herein, the terms "lean ethylene feedstock" or "pretreated ethylene feedstock" refer to dilute ethylene feeds that have been treated to reduce the higher olefin content to about 0.2–5%, preferably about 0.2–2%, by volume of ethylene content. Flowstream 26 leaving absorber 10 comprises rich benzene contaminated principally with higher olefins stripped from the dilute ethylene feedstock. As used herein, the term "rich benzene" refers to benzene which has been used to absorb higher olefins from a dilute ethylene feedstock and thus recovers a significant proportion on the order of about 96–99.8% of the higher olefins.

Alkylation reactor 12 is of conventional design utilizing a catalyst effective in promoting the alkylation of benzene with ethylene. Process parameters in reactor 12 are ialso conventional, and may be optimized by routine experimentation. The use of multiple ethylene feeds 30, 32 and 34, and multiple benzene feeds 40, 42 and 44, to reactor 12, as shown in FIG. 1, may improve efficiency. Dilute ethylene and benzene can also be premixed, as shown at stream 38, prior to introduction into reactor 12. In a preferred embodiment, benzene is alkylated with ethylene at moderate temperature and pressure over a suitable zeolite catalyst.

Flowstream 50 emerging from reactor 12 comprises primarily crude ethylbenzene, unreacted benzene, perhaps some unreacted ethylene, and a small proportion of $C_9$ and higher alkylaromatic compounds, and polyalkylated aromatic compounds, principally diethylbenzene. By utilizing greater than stoichiometric ratios of benzene to ethylene feed in reactor 12, for example between about a 4:1 to 9:1 overall molar ratio of benzene to ethylene, proper choice of alkylation catalyst, and optimization of other reaction parameters, it is possible to insure virtually complete conversion of ethylene. Stream 50 is then directed into a lower region of benzene fractionation column 14 where crude ethylbenzene and the higher alkylaromatic compounds are condensed out and withdrawn as flowstream 52. A stream 54 of make-up benzene is added to the upper region of column 14, as needed, to maintain steady-state conditions. As discussed above, rich benzene stream 26, contaminated with higher olefins, is also added to the upper region of column 14. In the middle region of column 14, flowstream 60 is removed as a liquid substantially free of olefins and used as the benzene feed back to absorber 10 and to alkylation reactor 12. Meanwhile, overhead flowstream 56 from column 14 is passed through a partial condenser (not shown) to remove a reflux liquid benzene stream 58 that may be returned to column 14, leaving a vapor stream 59 (see FIG. 2) comprising gaseous higher olefins and other vapor components which may be further treated as described hereinafter. Alternatively, the higher olefins, alkanes and hydrogen in stream 59 may be combusted as fuel to provide heat, for example for the feeds going to the alkylation reactor. As one consequence of this integrated process, this invention requires only a single unit operation, absorber 10, that is not part and parcel of the conventional ethylbenzene production. Furthermore, no foreign substances requiring special handling or posing contamination possibilities need to be introduced into the production environment.

Figure 2:
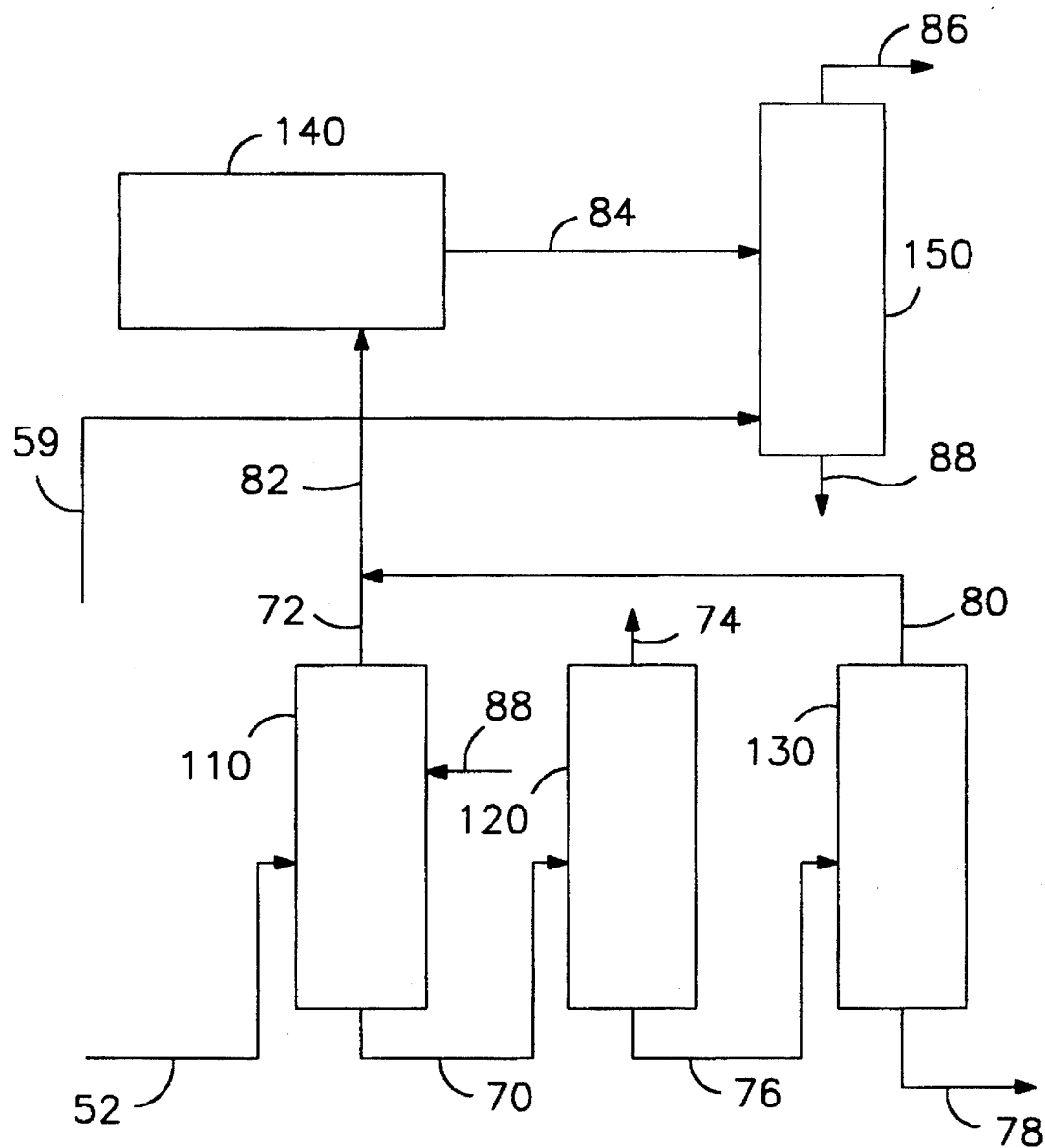
FIG. 2 is a partial schematic flowchart showing an optional downstream transalkylation process which can be readily integrated with the ethylbenzene process of this invention to realize additional efficiencies and advantages.

Additional synergies can be realized from integrating the process of this invention with a downstream transalkylation process as illustrated in FIG. 2. Thus, concentrated reactor effluent stream 52 containing crude ethylbenzene, about 20–80 wt. % benzene, and higher-boiling polyalkylated aromatics may be directed to a second benzene recovery column 110 to separate a crude ethylbenzene product stream 70 from a benzene stream 72. The crude ethylbenzene stream 70, including components such as cumene, n-propylbenzene, and other alkylaromatics heavier than ethylbenzene, plus other heavy material, is sent to a third fractionation column 120 in which an ethylbenzene product 74 is distilled overhead. A crude polyethylbenzene stream 76 is recovered from the bottom of column 120 and directed to a fourth fractionation column 130. In column 130, polyethylbenzenes, including diethylbenzene, cumene, n-propylbenzene, and other alkylaromatics heavier than ethylbenzene, are separated from heavy residue material 78, removed as overhead stream 80, and combined with at least a portion of benzene vapor stream 72 coming from column 110 to form a mixed stream 82. Mixed stream 82 is then fed to a secondary transalkylation reactor 140 operating in the vapor phase. In this secondary, transalkylation reactor, in the presence of a suitable catalyst and under proper reactor conditions, the transalkylation of diethylbenzene to ethylbenzene is promoted as well as the dealkylation of higher alkylbenzenes, such as cumene, and n-propylbenzene, to form benzene and light gases. Transalkylation product stream 84 from reactor 140, comprising ethylbenzene, benzene, light gases, and unreacted components, is :fed to a stabilizer/absorber unit 150. Vapor stream 59 coming from the partial condenser associated with column 14 may also be fed to stabilizer 150 to recover the aromatic components. The light gases 86 recovered from the stabilizer may be combusted as fuel. The stabilizer bottoms stream 88 may be returned to benzene recovery column 110, for example, for further recovery of benzene and ethylbenzene as described above.

Particularly when utilized in combination with the above-described downstream operations, the process of this invention is therefore extremely tolerant of and well adapted to the presence of greater than usual quantities of propylene and higher olefins in the ethylene feedstock. Thus, reaction byproducts resulting from the presence of such higher olefins are efficiently processed by such downstream treatment to recover additional ethylbenzene, recycle benzene, and fuel gas thereby minimizing material losses.

Figure 3:
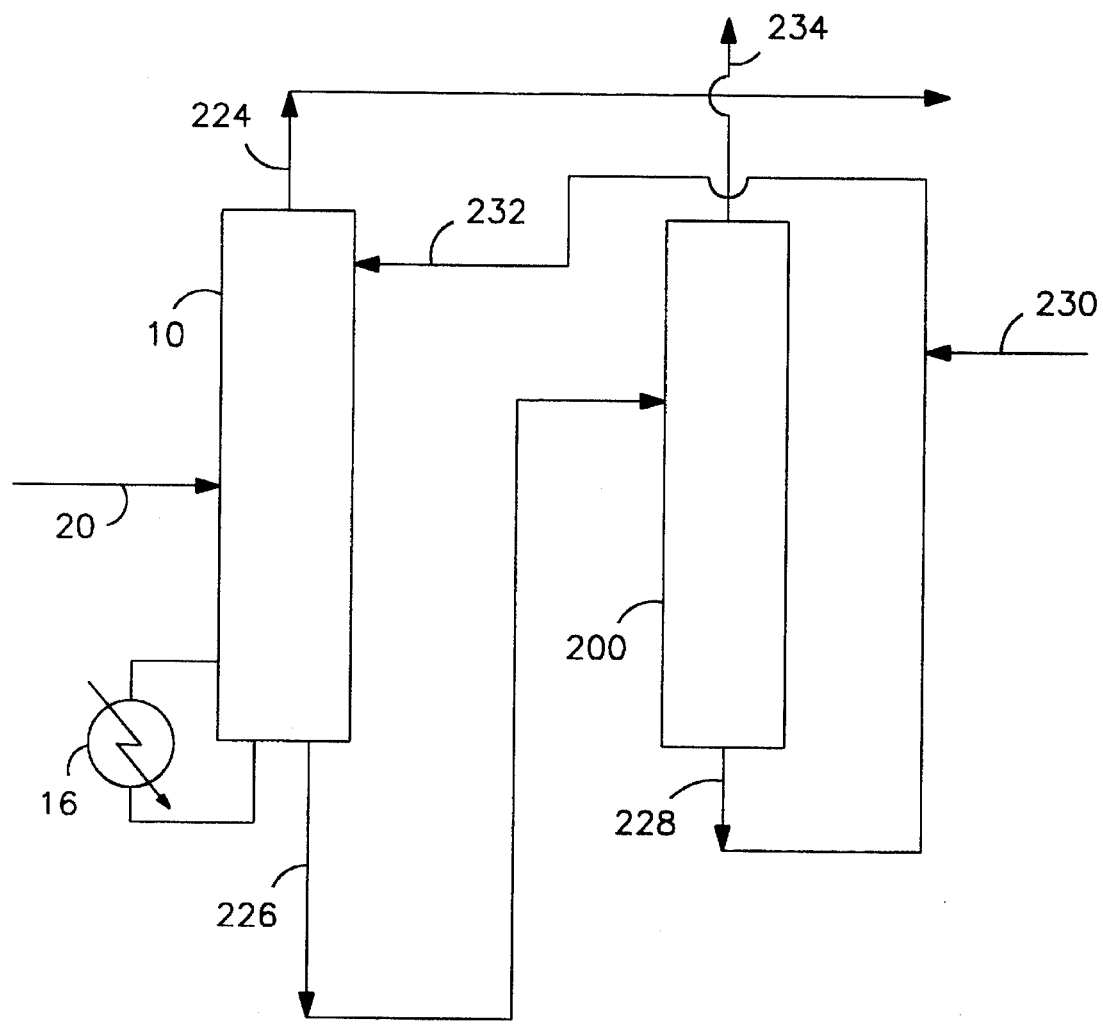
FIG. 3 is a partial schematic flowchart of an ethylbenzene production process utilizing ethylbenzene or a blend of ethylbenzene and benzene for the dilute ethylene feedstream pretreatment of this invention.

FIG. 3 illustrates an alternative embodiment of this invention wherein olefin components are scrubbed from a dilute ethylene feedstock utilizing ethylbenzene or a mixture of ethylbenzene and benzene obtained in whole or in part from a downstream operation in an ethylbenzene process. Thus, dilute ethylene feedstock 20 is directed into absorber column 10 as described above in connection with FIG. 1. In absorber 10, the dilute ethylbenzene feedstock is brought into contact with lean ethylbenzene or a mixture of lean benzene and ethylbenzene introduced to absorber 10 via feedstream 232. The ratio of benzene to ethylbenzene in feedstream 232 may range from 0% benzene/100% ethylbenzene to 100% benzene/0% ethylbenzene. The ratio of ethylbenzene or benzene-ethylbenzene mix to ethylene feedstock in absorber 10 may advantageously range from about 5–50, parts by weight.

Flowstream 224 leaving absorber 10 comprises a lean or pretreated ethylene feedstock having a reduced content of higher olefins and thus ready for feeding to the alkylation reactor. As used herein, the terms "lean ethylene feedstock" or "pretreated ethylene feedstock" refer to dilute ethylene feeds that have been treated to reduce the higher olefin content to about 0.2–5%, preferably about 0.2–2%, by volume of ethylene content. Flowstream 226 leaving absorber 10 comprises rich ethylbenzene or benzene-ethylbenzene mix contaminated principally with higher olefins stripped from the dilute ethylene feedstock. As used herein, the term "rich ethylbenzene" refers to ethylbenzene which has been used to absorb higher olefins from a dilute ethylene feedstock and thus recovers a significant proportion on the order of about 96–99.8% of the higher olefins.

Flowstream 226 may be directed to a stripper column 200 to separate the dissolved olefin components as an overhead vent stream 234, while recovering the ethylbenzene or benzene-ethylbenzene mix as bottoms stream 228 for recycle to absorber 10. Makeup ethylbenzene or benzene-ethylbenzene stream 230 is taken from a downstream operation, for example from ethylbenzene product stream 74 or from the stabilizer bottoms stream 88, both as seen in FIG. 2. In still a further embodiment of the invention, makeup stream 230 may also comprise diethylbenzene and other higher alkylaromatic compounds taken from a downstream stage of the ethylbenzene production, as described above.

The following hypothetical example is illustrative of the process of this invention and the type of results which can be realized thereby.

EXAMPLE

A dilute ethylene feedstock from a fluid catalytic cracking operation of a petroleum refinery is pretreated according to this invention to prepare it for use in ethylbenzene production. Initially the ethylene feedstock comprises 23.5 vol % ethylene, 3.0 vol % propylene, 1.0 vol % butylene, and less than 1.0 vol % higher olefins. In addition, the dilute ethylene feedstock comprises primarily nitrogen, hydrogen, methane, ethane, carbon dioxide and carbon monoxide. The dilute ethylene feedstock is pretreated by directing it into countercurrent contact with lean benzene in an absorber column. The temperature in the absorber column is maintained between about 40° C.–170° C., and the pressure is maintained at about 265 psig. Lean benzene is added to the absorber column at a rate sufficient to maintain a proportion of benzene to ethylene feedstock in the column of about 13 parts by weight. Rich benzene, containing propylene and other higher olefins, is removed from the absorber :Column and directed to the benzene fractionation column. A pretreated dilute ethylene feedstream is removed from the absorber column and directed to the alkylation reactor. The pretreated dilute ethylene feedstream contains 0.27 vol % propylene, 0.003 vol % butylene, and a negligible amount of higher olefins.

The foregoing example illustrates that the pretreatment process of this invention is effective in reducing the higher olefin content of a dilute ethylene stream to about 1% or less by volume of the ethylene content thereby rendering it suitable as the feedstream to the alkylation step of the ethylbenzene process, while adding only a single unit operation and readily integrating the pretreatment into conventional ethylbenzene production.

Since certain changes may be made in the above-described process without departing from the scope of the invention herein involved, it is intended that all matter contained in the above description shall be interpreted in an illustrative and not in a limiting sense.

Having described the invention, what I claim is:

1. In a process for preparing ethylbenzene by the catalytic alkylation of benzene with ethylene in an alkylation step carried out in a first alkylation reactor, the improvement comprising utilizing a scrubbing step for absorbing excessive quantities of higher olefins from a rich ethylene feedstock prior to the alkylation step by contacting the rich ethylene feedstock with a lean aromatic stream consisting essentially of benzene, ethylbenzene and mixtures thereof and thereafter separating a rich aromatic stream, together with said higher olefins, to create a lean ethylene feedstock, and directing Said lean ethylene feedstock to said first alkylation reactor.

2. Process according to claim 1 wherein said scrubbing step is carried out in an absorber column.

3. Process according to claim 2 wherein said rich ethylene feedstock and said lean aromatic stream are fed countercurrently through said column.

4. Process according to claim 1 wherein said scrubbing step is carried out at a temperature of about 40°–325° C. and at a pressure of about 100–400 psig.

5. Process according to claim 1 wherein the ratio of the lean aromatic stream to the rich ethylene feedstock in said scrubbing step is about 5 to 50 parts by weight.

6. Process according to claim 1 wherein the proportion of higher olefins is reduced to about 0.2 to 5% by volume of the ethylene content.

7. Process according to claim 1 wherein the proportion of higher olefins is reduced to about 0.2 to 2% by volume of the ethylene content.

8. Process according to claim 1 further comprising the step of directing said rich aromatic stream to at least a first fractionation column to separate a lean aromatic stream from said higher olefins.

9. Process according to claim 8 further comprising the step of recycling at least a portion of said lean aromatic stream from said first fractionation column back to said scrubbing step as a lean aromatic recycle stream.

10. Process according to claim 9 wherein said aromatic stream consists essentially of benzene, and further comprising the step of recycling lean benzene from said first fractionation column to said first alkylation reactor.

11. Process according to claim 10 further wherein multiple feedstreams of lean benzene are introduced at different locations along said first alkylation reactor.

12. Process according to claim 11 further wherein multiple feedstreams of lean ethylene feedstock are introduced at different locations along said first alkylation reactor.

13. Process according to claim 10 further comprising the steps of: recovering a concentrated reactor effluent comprising benzene, ethylbenzene, and polyalkylaromatics from said first fractionation column; treating said concentrated reactor effluent in a second fractionation column to separate benzene from a crude ethylbenzene stream; treating said crude ethylbenzene stream in a third fractionation column to separate ethylbenzene from a crude polyalkylaromatic stream; treating said crude polyalkylaromatic stream in a fourth fractionation column to separate a stream comprising diethylbenzene, cumene, n-propylbenzene and other heavy alkylaromatics from heavier residual components; combining said polyethyl-benzene stream with at least a portion of the benzene recovered from said second fractionation column and subjecting the combined stream to catalytic transalkylation conditions in a transalkylation reactor to form a transalkylation product stream comprising ethylbenzene, benzene, light gases, and unreacted components; and, separating the light gases from said transalkylation product stream and recycling the ethylbenzene and benzene components of said transalkylation product stream to said second fractionation column.

14. Process according to claim 13 further comprising the step of feeding the olefin stream from said first fractionation column and said transalkylation products stream to a stabilizer and absorber to separate the olefins and light gases from the ethylbenzene and benzene recycle stream.

15. Process according to claim 9 wherein said aromatic stream consists essentially of ethylbenzene, and further comprising the step of adding an ethylbenzene make-up stream to said lean aromatic recycle stream as needed to maintain said 5 to 50 parts by weight ratio in said scrubbing step, at least a portion of said ethylbenzene make-up stream being drawn from a downstream operation in said ethylbenzene process.

16. In a process for preparing ethylbenzene by contacting ethylene with benzene in a first alkylation reactor containing an alkylation catalyst and subsequently directing the reaction products to at least a first fractionation column to separate crude ethylbenzene and unreacted benzene from the olefin components, the improvements comprising: (a) utilizing a scrubbing step comprising absorbing excessive quantities of higher olefins from an untreated ethylene feedstock prior to the alkylation reactor by contacting said untreated ethylene feedstock with lean benzene and thereafter separating rich benzene, together with said higher olefins, to leave a treated ethylene feedstock; (b) directing said rich benzene to said first fractionation column to separate said higher olefins and recover lean benzene; and (c) directing said treated ethylene feedstock to said first alkylation reactor.

17. Process according to claim 16 wherein said scrubbing step is carried out by feeding said untreated ethylene feedstock and said lean benzene countercurrently through a column.

18. Process according to claim 16 wherein said scrubbing step is carried out at a temperature of about 40°–325° C. and at a pressure of about 100–400 psig.

19. Process according to claim 16 wherein the ratio of lean benzene to untreated ethylene feedstock in said scrubbing step is about 5–50 parts by weight.

20. Process according to claim 16 wherein the proportion of higher olefins is reduced to about 0.2 to 5% by volume of the ethylene content.

21. Process according to claim 16 wherein the proportion of higher olefins is reduced to about 0.2 to 2% by volume of the ethylene content.

22. Process according to claim 16 further comprising the step of recycling lean benzene from said first fractionation column to said scrubbing step.

23. Process according to claim 16 further comprising the step of recycling lean benzene from said first fractionation column to said scrubbing step and to said first alkylation reactor.

24. Process for treating a dilute ethylene stream containing higher olefins to reduce said higher olefin content comprising the steps of contacting said ethylene stream with a lean aromatic stream consisting essentially of benzene, ethylbenzene, and mixtures thereof in the absence of any alkylation catalyst under conditions sufficient to bring the higher olefin content of the ethylene stream to about 0.2 to 5% by volume of the ethylene content and thereafter separating a rich aromatic stream, together with said higher olefins, from said ethylene stream.

25. Process according to claim 24 wherein said aromatic stream consists essentially of benzene.

26. Process according to claim 24 wherein said aromatic stream consists essentially of ethylbenzene.

27. Process according to claim 24 wherein said aromatic stream consists essentially of a mixture of benzene and ethylbenzene.

28. Process for preparing ethylbenzene comprising the following steps:
(a) pretreating a dilute ethylene feedstock contaminated with higher olefins by contact with lean benzene to reduce the higher olefins content of said feedstock and to produce rich benzene and a lean ethylene feedstock;
(b) directing said rich benzene from step (a) to a first fractionation column to separate lean benzene and crude ethylbenzene from said higher olefins;
(c) contacting said lean ethylene feedstock from step (a) and at least a portion of said lean benzene from step (b) in the presence of an alkylation catalyst at alkylation temperature and pressure so as to form ethylbenzene;
(d) directing at least a portion of said lean benzene from step (b) to said ethylene pretreatment of step (a);
(e) directing at least a portion of the alkylation reaction products of step (c) to said first fractionation column; and
(f) withdrawing crude ethylbenzene from a first region of said first fractionation column and a stream containing higher olefins from a second region of said first fractionation column.

29. Process according to claim 28 further comprising the steps of:
(g) treating the crude ethylbenzene product of step (f) to separate a stream of benzene therefrom;
(h) treating the crude ethylbenzene product of step (g) to separate a stream of higher alkylaromatic compounds therefrom;
(i) combining the stream of higher alkaromatic compounds from step (h) with the stream of benzene from step (g);
(j) subjecting the combined stream of step (i) to catalytic transalkylation conditions to form a transalkylation product stream; and
(k) directing at least a portion of said transalkylation product stream to the treatment process of step (g).

30. Process according to claim 29 wherein said stream of higher alkylaromatic compounds comprises diethylbenzene, cumene and n-propylbenzene.

31. Process according to claim 30 wherein said catalytic transalkylation conditions promote the transalkylation of said diethylbenzene to ethylbenzene, and the dealkylation of the heavier alkylaromatics to benzene and the respective alkenes.

32. Process according to claim 29 wherein the light gas components of said transalkylation product stream are separated from the ethylbenzene and benzene components in an absorber-stabilizer, and said ethylbenzene and benzene components are recycled to the treatment process of step (g).

33. Process according to claim 32 further wherein said higher olefins from step (b) are also fed to said absorber-stabilizer.

34. Process according to claim 1 further comprising the step of directing said rich aromatic stream to a stripper column to separate a lean aromatic stripper stream from said higher olefins.

35. Process according to claim 34 further comprising the step of recycling at least a portion of said lean aromatic stripper stream from said stripper column to said scrubbing step as a lean aromatic recycle stream.

36. Process according to claim 34 further wherein at least a portion of said lean aromatic stripper stream is mixed with a makeup stream consisting essentially of benzene, ethylbenzene and mixtures thereof to form a lean aromatic recycle stream which is recycled to said scrubbing step.

* * * * *

UNITED STATES PATENT AND TRADEMARK OFFICE
CERTIFICATE OF CORRECTION

PATENT NO.   : 5,602,290
DATED        : February 11, 1997
INVENTOR(S)  : Kevin J. Fallon It is certified that error appears in the above-indentified patent and that said Letters Patent is hereby corrected as shown below:

Col. 1, line 52 - "Buffer" should be -- Butler --.

Col. 3, line 20 - delete the "0" before "ethylbenzene".

Col. 5, line 3 - the word "ialso" should be -- also --.

Col. 5, line 39 - the word "cornbusted" should be -- combusted --.

Col. 6, line 10 - the word ":fed" should be -- fed --.

Col. 6, line 41 - the comma "," after the numeral "50" should be deleted.

Col. 7, line 27 - the word ":Column" should be -- column --.

Col. 7, line 58 - the word "Said" should be -- said --.

Col. 8, line 40 - the word "polyethyl-benzene" should be -- polyethylbenzene --.

Signed and Sealed this

First Day of July, 1997

Attest:

BRUCE LEHMAN

Attesting Officer

Commissioner of Patents and Trademarks